(12) United States Patent
Christiansen et al.

(10) Patent No.: US 6,238,367 B1
(45) Date of Patent: May 29, 2001

(54) ELECTRICAL CONNECTOR FOR TRANSDUCER OF IMPLANTABLE DRUG INFUSION DEVICE

(75) Inventors: Chris C. Christiansen, Oakdale; James M. Olsen, Plymouth, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/561,538

(22) Filed: Apr. 28, 2000

(51) Int. Cl.[7] ................................. A61M 11/00
(52) U.S. Cl. ................... 604/93; 128/DIG. 12; 604/891.1
(58) Field of Search ............... 64/93.01, 30, 31, 64/65, 151, 66, 175, 67, 70, 890.1, 891.1, 892.1; 128/DIG. 12, DIG. 13

(56) References Cited

U.S. PATENT DOCUMENTS

| 4,692,147 | 9/1987 | Duggan | 604/93 |
| 5,840,069 | 11/1998 | Robinson | 604/131 |
| 6,036,459 | 3/2000 | Robinson | 417/477.7 |

OTHER PUBLICATIONS

"Piezoelectric Acoustic Generators," AVX–Kyocera Co. product sheet.

*Primary Examiner*—Manuel Mendez
(74) *Attorney, Agent, or Firm*—Banner & Witcoff, Ltd.

(57) ABSTRACT

An implantable drug infusion device includes a bulkhead having a chamber and a shield for the bulkhead. A transducer is secured to the shield. An electronic module is located in the bulkhead for controlling operation of a pump assembly. A biasing member is in electrical contact with the electronic module and the transducer such that current transmitted from the electronic module to the transducer through the biasing member actuates the transducer.

13 Claims, 3 Drawing Sheets

ELECTRICAL CONNECTOR FOR TRANSDUCER OF IMPLANTABLE DRUG INFUSION DEVICE

BACKGROUND OF THE INVENTION

1. Field of the Invention

The present invention relates to an implantable drug delivery device having a transducer, and more particularly, relates to an improved connection between a transducer and an electronic module which controls operation of an implantable drug delivery device.

2. Description of the Related Art

Implantable drug infusion devices are well known in the art. These devices typically include a medication reservoir within a generally cylindrical housing or bulkhead. Some form of fluid flow control is also provided to control or regulate the flow of fluid medication from the reservoir to the outlet of the device for delivery of the medication to the desired location in a body, usually through a catheter. These devices are used to provide patients with a prolonged dosage or infusion of a drug or other therapeutic agent.

Active drug infusion devices feature a pump or a metering system to deliver the drug into the patient's system. An example of such a drug infusion pump currently available is the Medtronic SynchroMed programmable pump. Additionally, U.S. Pat. No. 4,692,147 (Duggan), U.S. Pat. No. 5,840,069 (Robinson), and U.S. Pat. No. 6,036,459 (Robinson), assigned to Medtronic, Inc., Minneapolis, Minn., disclose body-implantable electronic drug administration devices comprising a peristaltic (roller) pump for metering a measured amount of drug in response to an electronic pulse generated by control circuitry associated within the device. Each of these patents is incorporated herein by reference in their entirety for all purposes.

A prior art implantable device 2 is shown in FIG. 1 and includes a bulkhead 4 housing a peristaltic pump 6, a motor 8, and batteries 10, 12. A bulkhead, when used herein, refers to the central structure or chassis for an implantable drug infusion device. An electronic module 14 controls operation of pump 6 and motor 8. A fill port 18 is used to inject drug into a drug reservoir (not shown), and a catheter port 20 is used to transport the drug from the reservoir via the pump to a patient's anatomy. The bulkhead is covered by a shield 24. A transducer 26 is secured to an underside of shield 24, and provides an audible output when excited by an electrical signal. Transducer 26 is connected by wire 28 to output terminal 9 of electronic module 14.

The prior art delivery devices, however, are limiting in that the wire which connects the transducer to the output terminal of the electronic module is first soldered to the transducer and then resistance welded to the output terminal. As the device is assembled, the wire must be carefully tucked into place before the shield can be positioned on the bulkhead. The wire used is typically platinum, which is very expensive. Thus, connecting transducers to an electronic module in prior art devices is both difficult and expensive.

It is an object of the present invention to provide an implantable drug infusion device which reduces or wholly overcomes some or all of the difficulties inherent in prior known devices. Particular objects and advantages of the invention will be apparent to those skilled in the art, that is, those who are knowledgeable or experienced in this field of technology, in view of the following disclosure of the invention and detailed description of preferred embodiments.

SUMMARY OF THE INVENTION

The present invention provides an implantable drug infusion device which features an electrically conductive biasing member positioned between a shield and a electronic module of the device to simplify the assembly of the device.

In accordance with a first aspect, an implantable drug infusion device includes a bulkhead, and a shield for the bulkhead. A transducer is secured to and in electrical contact with the shield. An electronic module is located in the housing for controlling operation of a pump assembly. A biasing member is in electrical contact with the electronic module and the transducer such that current transmitted from the electronic module to the transducer through the biasing member actuates the transducer.

In accordance with another aspect, an implantable drug infusion device includes a bulkhead and a shield for covering the bulkhead. An electronic module is located in the bulkhead for controlling operation of a pump assembly. An electrically conductive pin is formed on the electronic module. A transducer is secured to and in electrical contact with the shield. A first end of a coil spring is secured to the pin. A second end of the coil spring extends substantially axially away from the coil spring and contacts the transducer such that current transmitted from the electronic module to the transducer through the coil spring actuates the transducer.

In accordance with yet another aspect, an implantable drug infusion device includes a bulkhead having a race. A pump tube has an inlet and an outlet and is positioned within the race. A motor assembly is positioned within the bulkhead. A pumphead assembly is positioned within the bulkhead, and the motor assembly drives the pumphead assembly. A battery is positioned within the bulkhead and provides a power source to the motor assembly. An electronic module is positioned within the bulkhead and has a pin connector thereon. A shield covers the bulkhead, and a transducer is secured to and in electrical contact with shield. An electrically conductive coil spring is press-fit at a first end thereof to the pin connector. A second end of the coil spring has a pigtail formed thereon, with the pigtail contacting the transducer when the shield is on the bulkhead in an assembled condition such that current transmitted from the electronic module to the transducer through the coil spring actuates the transducer.

From the foregoing disclosure, it will be readily apparent to those skilled in the art, that is, those who are knowledgeable or experienced in this area of technology, that the present invention provides a significant advance over the prior art. Preferred embodiments of the implantable infusion device of the present invention can make it significantly easier to connect a transducer to an electronic module, and reduce the costs associated with connecting the transducer. These and additional features and advantages of the invention disclosed here will be further understood from the following detailed disclosure of preferred embodiments.

BRIEF DESCRIPTION OF THE DRAWINGS

Preferred embodiments are described in detail below with reference to the appended drawings. The accompanying drawings, which are incorporated into and form a part of this specification, together with the description, serve to explain the principles of the invention. The drawings are not drawn necessarily to scale, are only for the purpose of illustrating a preferred embodiment of the invention, and are not to be construed as limiting the invention. Some features of the implantable drug infusion device depicted in the drawings have been enlarged or distorted relative to others to facilitate explanation and understanding. The above mentioned and other advantages and features of the invention will become apparent upon reading the following detailed description and referring to the accompanying drawings in which like numbers refer to like parts throughout and in which.

DESCRIPTION OF THE PREFERRED EMBODIMENTS

Figure 1:
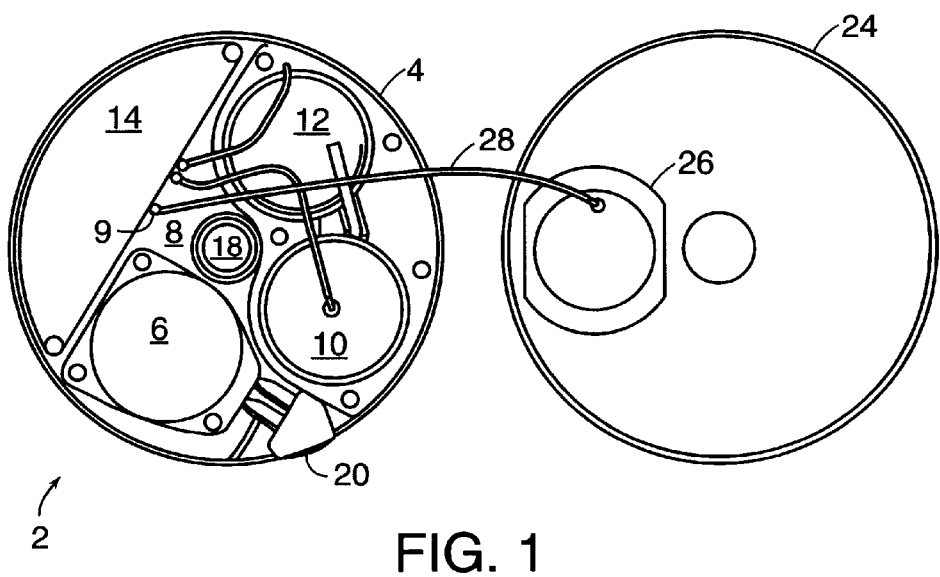
FIG. 1 is a plan view of an implantable drug infusion device of the prior art, shown prior to the shield being secured to the bulkhead.
Figure 2:
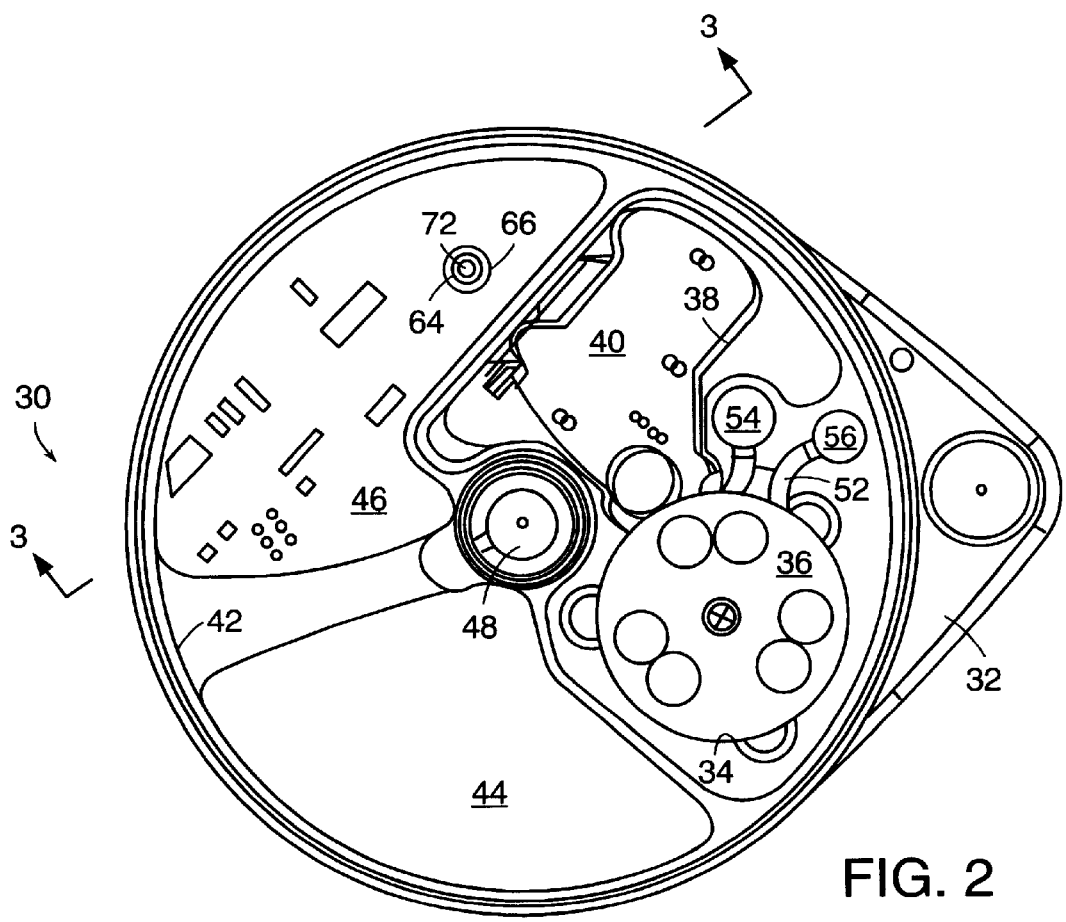
FIG. 2 is plan view of an implantable drug infusion device of the present invention.

As shown in FIG. 2, an implantable drug infusion device 30 in accordance with the invention comprises a bulkhead 32 containing a number of chambers and cavities sized and configured to house various subsystems of the implantable drug infusion device. In particular, bulkhead 32 has a first chamber 34 sized and configured to house a peristaltic pumphead assembly 36. A second chamber 38 is sized and configured to house a motor assembly 40 which drives pumphead assembly 36. An exemplary motor assembly comprises a stepper motor which responds to pulses to drive the pumphead assembly. A third chamber 42 houses a battery 44 to provide a power source for motor assembly 40, and an electronic module 46. The term "electronic module" as used herein, refers to a control unit which controls operation of the motor assembly 40 and pumphead assembly 36. A typical electronic module consists of a microprocessor based printed circuit board. The electronic module can be programmed to change parameters of the device, e.g., alter the duration of stepper motor drive pulses, vary the delay time between motor pulses, and vary the number of motor pulses to be dispensed for a particular dosage of drug. The electronic module can also transmit alarm signals indicating problem conditions, e.g., low volume of drug in the reservoir or a low battery level.

Bulkhead 32 has an integral fill port cavity 48, sized and configured to house a septum and components to retain the septum. Drugs are injected through the septum to fill a reservoir (not shown) contained within a lower portion of bulkhead 32. A pathway is formed between the reservoir and a pump inlet cavity 54, through which drugs are introduced into a pump tube 52. Pumphead assembly 36 includes a compression member (not shown), such as a roller arm assembly for compressing pump tube 52 against the wall of chamber 34, thereby forcing medication to move through the tube in a known peristaltic manner. The drugs exit pump outlet cavity 56 and travel through another pathway formed in bulkhead 32 to a catheter port on the periphery of bulkhead 32 from which the drug exits the device 30 and enters the anatomy of the individual. The structure of the septum, retaining components, and pathways, and catheter port are known to one of skill in the art and are not shown here.

Figure 3:
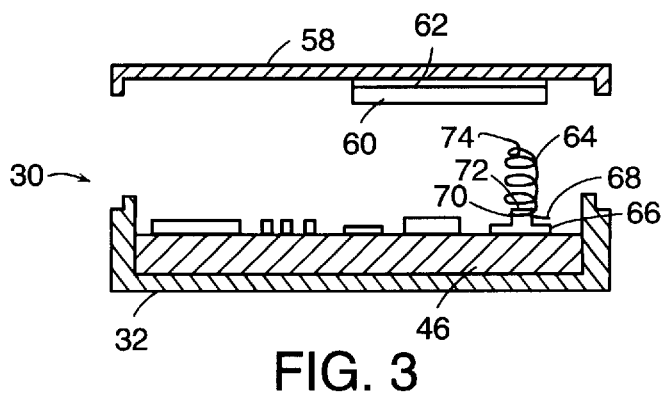
FIG. 3 is a section view, taken along lines 3—3 of FIG. 2, of the bulkhead of the implantable device of FIG. 2 and a shield for the bulkhead, shown prior to the shield being secured to the bulkhead.

A shield 58, seen in FIG. 3, is also provided as a cover for bulkhead 32 to provide protection for the components of drug infusion device 30. Shield 58 is preferably formed of titanium or other similar non-magnetic material, as are other parts of the device which are exposed to body tissue and fluids. A transducer 60 is secured to an under surface of shield 58 with an electrically conductive epoxy 62. Shield 58 is excited by transducer 60 to facilitate transmission of audio energy from the body. Transducer 60 is suitable for producing an audio output audible outside the body when excited by an electrical signal in the audio range. Transducer 60 typically includes a piezoelectric ceramic mounted on a metal diaphragm, the ceramic expanding and contracting upon application of an AC voltage and causing the metal diaphragm to bend and produce sound waves in known fashion. Transducers for such applications are well known in the art and further description will not be provided here.

Figure 4:
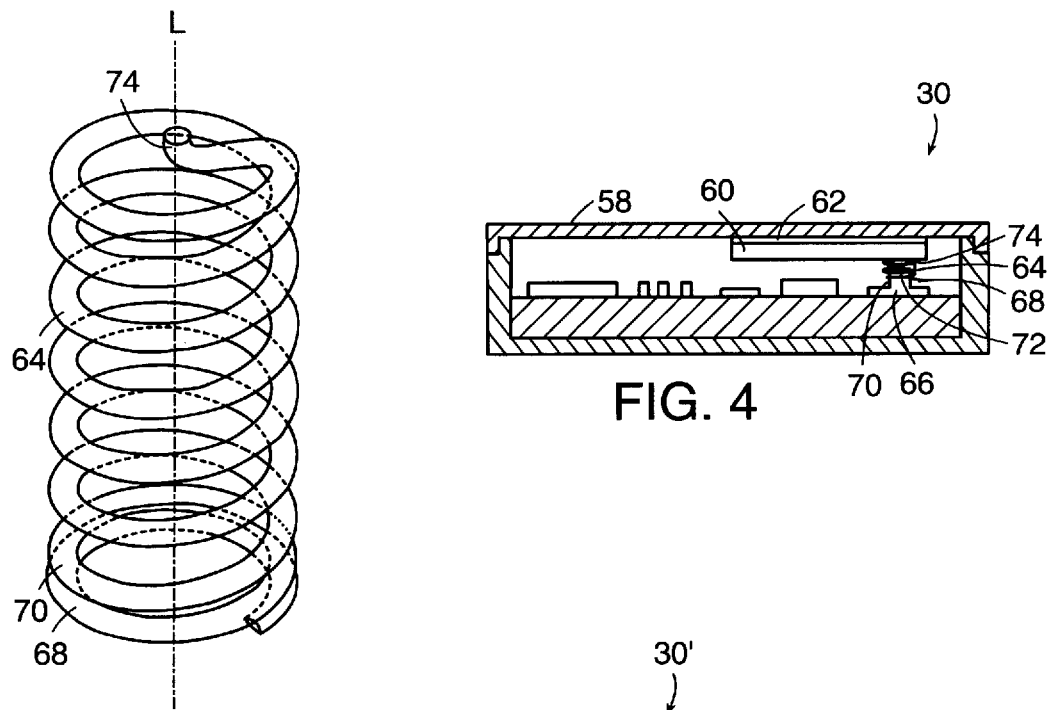
FIG. 4 is a section view, similar to FIG. 3, showing the implantable device in its assembled state.

Shield 58 is shown in FIG. 3 in position just prior to being placed on bulkhead 32. An electrically conductive biasing member such as coil spring 64 is secured to an output terminal 66 of electronic module 46. When shield 58 is placed on bulkhead 32, as seen in FIG. 4, coil spring 64 contacts transducer 60, providing a pathway to transmit a signal from electronic module 46 to transducer 60. In a preferred embodiment, coil spring 64 contacts transducer 60 proximate an external peripheral edge of transducer 60. This provides for the maximum deflection of transducer 60, and, therefore, provides the largest possible audible signal.

To assemble drug infusion device 30, shield 58 is positioned on and clamped to bulkhead 32. A signal is then sent to transducer 60 via coil spring 64 in order to ensure the transducer is functioning properly. Upon hearing an audible signal from the transducer, shield 58 is welded to bulkhead 32. In a preferred embodiment, the contact force exerted by coil spring 64 on transducer 60 is approximately 25–100 g, and the current transmitted through coil spring 64 is approximately <1 milliamp.

The placement of coil spring 64 on electronic module 46 in a known location ensures that the spring will contact transducer 60 when shield 58 is properly positioned on bulkhead 32, thereby simplifying the assembly process for the implantable device and reducing manufacturing costs.

In the illustrated embodiment, coil spring 64 is shown as being secured to output terminal 66, and contacting transducer 60 when shield 58 is positioned on bulkhead 32 in the assembled state. It is to be appreciated that coil spring 64 could alternatively be secured to transducer 60 and contact an output terminal on electronic module 46 when shield 58 is positioned on bulkhead 32 in its assembled state.

In other preferred embodiments, transducer 60 may be isolated from, rather than in electrical contact with, shield 58. In such embodiments, a second electrical connection, in addition to the electrically conductive biasing member, must be made between electronic module 46 and transducer 60 in order to complete the electrical circuit necessary to actuate transducer 60. The second electrical connection may be, for example, another electrically conductive biasing member.

Figure 5:
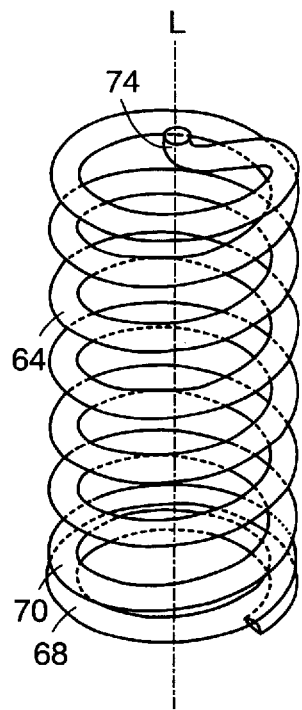
FIG. 5 is a perspective view of a coil spring of the implantable device of FIG. 2.

In a preferred embodiment, a first and second coil 68, 70 at a lower end of coil spring 64, seen more clearly in FIG. 5, form a closed coil, that is, they are stacked in abutting relationship, and are press-fit onto a pin 72 of output terminal 66, as seen in FIG. 3. An upper end of coil spring 64 has a pigtail 74 which is coaxial with longitudinal axis L of coil spring 64 and forms a point contact for abutment with transducer 60. By providing pigtail 74 in the center of coil spring 64, a symmetrical force is exerted on transducer 60 by coil spring 64. In a preferred embodiment, coil spring 64 is formed of phosphor bronze, beryllium copper, or brass, and would be appropriately plated, e.g., nickel/gold (underlayment/interface surface). Plating provides resistance to environmental attack (nobility), resistance to wear, and ductility.

Figure 6:
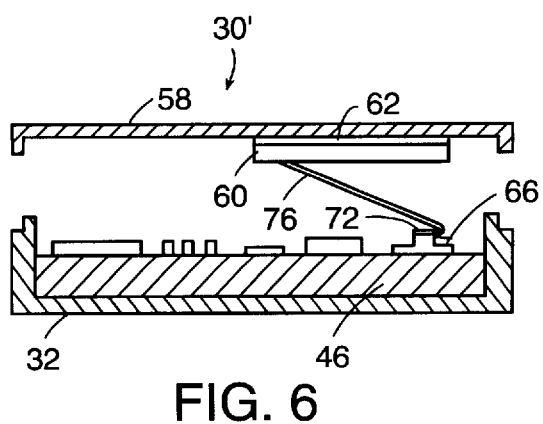
FIG. 6 is a section view, showing an alternative embodiment of the biasing member of the implantable device of FIG. 2.

In another preferred embodiment, shown in FIG. 6 in a partially assembled state, the biasing member comprises an electrically conductive cantilever arm 76. Cantilever arm 76 is secured at a first end to pin 72 of output terminal 66. When shield 58 is secured to bulkhead 32, cantilever arm 76 is compressed, thereby exerting a force on transducer 60 and providing an electrical path between transducer 60 and electronic module 46. It is to be appreciated that a cantilever arm could alternatively be secured at one end to transducer 60 and come into contact with electronic module 46 when shield 58 is placed on and secured to bulkhead 32. Cantilever arm 76 is preferably a flexible strip of metal, e.g., phosphor bronze, beryllium copper, or brass, and would be appropriately plated, e.g., nickel/gold (underlayment/ interface surface). Plating provides resistance to environmental attack (nobility), resistance to wear, and ductility.

Figure 7:
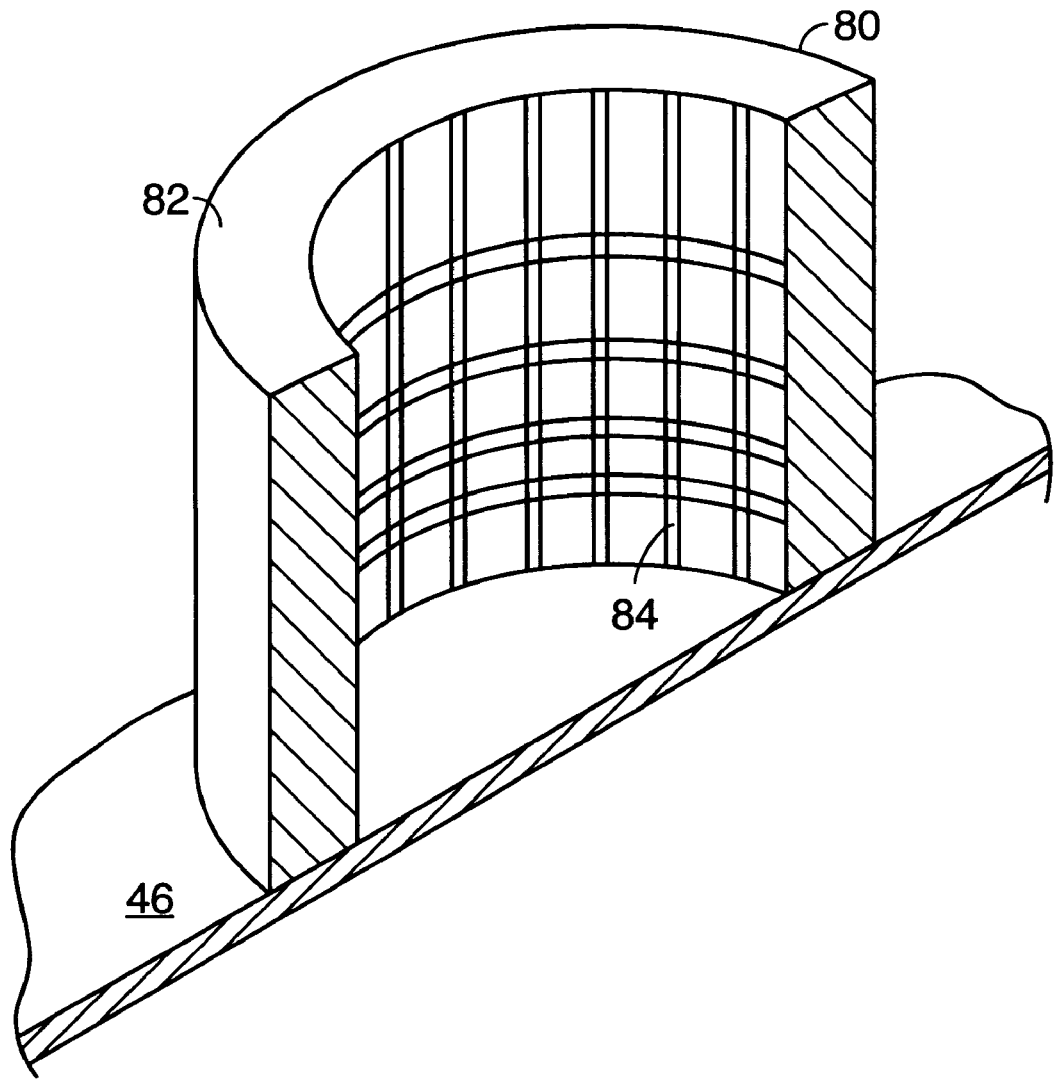
FIG. 7 is a section view, showing another alternative embodiment of the biasing member of the implantable device of FIG. 2.

In another preferred embodiment, shown in FIG. 7, a biasing member 80 comprises an elastomeric material 82 and an electrically conductive member or wire mesh 84. In the illustrated embodiment, biasing member 80 has a cylindrical shape and wire mesh 84 is disposed on an inner surface of the elastomeric material 82. However, it is to be appreciated that other shapes will be suitable, and that wire mesh 84 may be disposed on any surface of the elastomeric material 82, or totally contained within the material. Suitable shapes for the elastomeric material and locations for the conductive member will be readily apparent to those skilled in the art, given the benefit of this disclosure. Elastomeric member 80 provides a resilient contact force and an electrical contact between electronic module 46 and transducer 60. Elastomeric material 82 may be, e.g., a compressible foam or silicone. Similar elastomeric materials having an electrically conductive member therein are used in cell phone technology.

In light of the foregoing disclosure of the invention and description of the preferred embodiments, those skilled in this area of technology will readily understand that various modifications and adaptations can be made without departing from the scope and spirit of the invention. All such modifications and adaptations are intended to be covered by the following claims.

What is claimed is:

1. An implantable drug infusion device comprising, in combination:
   a bulkhead;
   a shield for the bulkhead;
   a transducer secured to the shield;
   an electronic module located in the bulkhead for controlling operation of a pump assembly;
   a biasing member in electrical contact with the electronic module and the transducer such that current transmitted from the electronic module to the transducer through the biasing member actuates the transducer.

2. The implantable drug infusion device of claim 1, wherein the biasing member comprises a coil spring.

3. The implantable drug infusion device of claim 2, wherein the coil spring includes a pigtail at one end thereof.

4. The implantable drug infusion device of claim 2, wherein the electronic module includes a pin connector and the coil spring is press-fit onto the pin connector.

5. The implantable drug infusion device of claim 1, wherein the biasing member comprises a cantilever arm.

6. The implantable drug infusion device of claim 1, wherein the biasing member comprises a flexible strip of metal.

7. The implantable drug infusion device of claim 1, wherein the biasing member contacts the transducer proximate a peripheral edge of the transducer.

8. The implantable drug infusion device of claim 1, wherein the transducer is in electrical contact with the shield.

9. The implantable drug infusion device of claim 1, wherein the transducer is secured to the shield with an electrically conductive epoxy.

10. The implantable drug infusion device of claim 1, wherein the biasing member is formed of elastomeric material and has an electrically conductive member contained therein.

11. An implantable drug infusion device comprising, in combination:
    a bulkhead;
    a shield for covering the bulkhead;
    an electronic module located in the bulkhead for controlling operation of a pump assembly;
    an electrically conductive pin on the electronic module;
    a transducer secured to and in electrical contact with the shield;
    a coil spring, a first end of the coil spring secured to the pin and a second end of the coil spring extending substantially axially away from the coil spring and contacting the transducer such that current transmitted from the electronic module to the transducer through the coil spring actuates the transducer.

12. The electrical connection of claim 11, wherein the biasing member contacts the transducer proximate a peripheral edge of the transducer.

13. An implantable drug infusion device comprising, in combination:
    a bulkhead having a race;
    a pump tube having an inlet and an outlet and being positioned within the race;
    a motor assembly positioned within the bulkhead;
    a pumphead assembly positioned within the bulkhead, the motor assembly driving the pumphead assembly;
    a battery positioned within the bulkhead, the battery providing a power source to the motor assembly;
    an electronic module positioned within the bulkhead and having a pin connector thereon;
    a shield to cover the bulkhead;
    a transducer secured to and in electrical contact with shield;
    an electrically conductive coil spring press-fit at a first end thereof to the pin connector,
    wherein a second end of the coil spring has a pigtail formed thereon, the pigtail contacting the transducer when the shield is on the bulkhead in an assembled condition such that current transmitted from the electronic module to the transducer through the coil spring actuates the transducer.

* * * * *